United States Patent [19]
Segal et al.

[11] Patent Number: 6,046,176
[45] Date of Patent: Apr. 4, 2000

[54] CHITIN EXTRACT FOR TREATMENT OF SKIN DISEASE

[75] Inventors: Esther Segal; Sarah Brenner, both of Tel-Aviv, Israel

[73] Assignee: Ramot University Authority for Applied Research and Industrial Development, Ltd., Ramat-Aviv, Israel

[21] Appl. No.: 09/011,654

[22] PCT Filed: Aug. 13, 1996

[86] PCT No.: PCT/IL96/00081

§ 371 Date: Apr. 24, 1998

§ 102(e) Date: Apr. 24, 1998

[87] PCT Pub. No.: WO96/06770

PCT Pub. Date: Feb. 27, 1997

[30] Foreign Application Priority Data

Aug. 14, 1995 [IL] Israel ............................................ 114923

[51] Int. Cl.$^7$ ............................. A61K 31/73; A61K 6/00; C08B 37/08
[52] U.S. Cl. ............................. 514/55; 536/20; 424/401; 424/70.1; 424/78.03; 424/78.07
[58] Field of Search .................. 514/55; 536/20; 424/401, 70.1, 78.03, 78.07

[56] References Cited

U.S. PATENT DOCUMENTS 4,035,267  7/1977  Glecker et al. .......................... 132/202
4,701,444  10/1987  Segal et al. ............................... 514/55
4,931,271  6/1990  Lang et al. ................................. 424/47
5,082,660  1/1992  Ounanian et al. ......................... 424/63

OTHER PUBLICATIONS

Saunders, Andrew's Diseases of the Skin, 8$^{tth}$ Ed. (1990), Chapter 10, pp. 194–198.
Ashbee et al., British J. of Dermatol., 129:533–540 (1993).
Danker et al., Reviews of Infectious Dis., 9:743–753 (Jul.–Aug. 1987).
Beachey et al., Current Concepts, Bacterial Adherence in Infectious Diseases, p. 5, 1982.
Segal, Microbiol. Sciences,4:344–347 (1987).
Faergemann et al., Arch Derm. Res., 275:246–250 (1983).
Simmons et al., Mycologia, 79:38–43 (1987).

*Primary Examiner*—Kathleen K. Fonda
*Attorney, Agent, or Firm*—Birch, Stewart, Kolasch & Birch, LLP

[57] ABSTRACT

A pharmaceutical composition for use in the prevention of or in the treatment of infection by yeasts of the genus Malassezia comprises a chitin soluble extract (CSE), optionally together with a suitable pharmaceutical carrier. The composition is particularly useful for the treatment and prevention of Seborrheic dermatitis. Also described is a method for treating or preventing the Seborrheic dermatitis caused by yeasts of the genus Malassezia comprising the step of topically applying the pharmaceutical composition of the invention to the area infected by or susceptible to infection by the yeasts.

9 Claims, No Drawings

CHITIN EXTRACT FOR TREATMENT OF SKIN DISEASE

This application is the national phase under 35 U.S.C. §371 of prior PCT International Application No. PCT/IL 96/00081 which has an International filing date of Aug. 13, 1996 which designated the United States of America, the entire contents of which are hereby incorporated by reference.

FIELD OF THE INVENTION

The present invention relates to pharmaceutical and cosmetic compositions based on a chitin extract for use in the prevention and treatment of skin diseases in general, and Seborrheic dermatitis in particular. The invention also relates to a method of treatment using such compositions.

BACKGROUND OF THE INVENTION

One of the more widespread skin diseases is Seborrheic dermatitis (hereinafter "SD") [1]. SD results in the shedding of small skin scales and mainly affects the scalp, eyebrows, eyelashes, ears, armpits and other folds in the skin. The shedding of skin scales from the scalp, known as dandruff, can have a serious effect on the aesthetic appearance of a person, and numerous lotions and shampoos are available to treat this affliction.

Although the etiology of this syndrome is not completely clear, recent evidence has indicated that the lipophilic yeast Malassezia furfur (syn. *Pityrosporum orbiculare*) is associated with this disease [2]. This yeast was also shown to cause fungemia and pulmonary infections in debilitated individuals, and particularly in neonates and adults receiving intralipid [3]. This led to the use of antimycotics, such as ketoconazole, as therapy for SD. However, since ketoconazole is a prescription drug, its use for the treatment of SD has been limited. An inexpensive, non-prescription formulation would therefore be desirable for the treatment of SD.

It is known that the first step in the development of an infection is the adherence of the microorganism to the host's epithelial cells [4]. This has also been confirmed for fungi in general [5], and for the yeast *Pityrosporum orbiculare* in particular [6].

A few years ago, a substance named chitin soluble extract (hereinafter "CSE") was found to be effective in the prevention of infections caused by yeasts of the genus Candida. CSE is described in U.S. Pat. No. 4,701,444 issued Oct. 20, 1987, whose contents are incorporated herein by reference. CSE was found to interfere with the adherence of Candida to epithelial cells, thus preventing the initiation of infection.

CSE can be prepared from commercially available chitin. The substance is applied topically to various tissues in order to prevent adherence of the pathogenic yeast, thereby reducing the rate of infection.

SUMMARY OF THE INVENTION

It is an object of the present invention to provide a pharmaceutical or cosmetic composition useful in the prevention and treatment of SD.

It is a further object of the present invention to provide a method of prevention and treatment of SD using such a composition.

According to one aspect of the present invention, there is provided a pharmaceutical composition for use in the prevention of or in the treatment of infection by yeasts of the genus Malassezia comprising CSE together with a suitable pharmaceutical carrier.

In a preferred embodiment of the present invention, the composition is used to prevent or treat Seborrheic dermatitis.

According to another aspect of the present invention, there is provided a method for treating or preventing the infection Seborrheic dermatitis caused by yeasts of the genus Malassezia comprising the step of applying a pharmaceutical composition according to the invention to the area infected by or susceptible to infection by the yeasts.

Although CSE was known previously to be effective in the prevention of Candida infection, it has now surprisingly been found that CSE is also effective against Malassezia infections. This result is quite unexpected in view of the major differences between these two species.

Candida has been found to be related to the Ascomycetes, while Malassezia is believed to be related to the Basidiomycetes [7]. Candida reproduce asexually by multilateral budding and form pseudohyphae (elongation of buds which do not separate from the mother cell and remain in chains resembling hyphae) and true mycelia. Some of the species (e.g. *C. krusei, C. quilliermondii C. lusitaniae*) also reproduce sexually via ascospore formation. Malassezia, on the other hand, reproduce by unipolar bud fission. The junction between the bud and the mother cell is broad and not constricted as in the genus Candida.

Candida sp. grow readily at a wide range of temperatures (both at room temperature (25–28° C.) and at 35–37° C.) on regular mycological media in the form of budding yeasts (blastospores), and also in hyphal form on specific media. Candida sp. can utilize a great variety of carbohydrates by the oxidative pathway ("assimilation") and anaerobic glycolysis ("fermentation"). *M. furfur*, on the other hand, shows generally no growth on regular mycological media and under conditions in which Candida can be grown. It has a requirement for long chain fatty acids, and grows preferably at 35° C.–37° C. on media supplemented with olive oil. Malassezia sp. are, contrary to Candida sp., nonfermentative and urease positive. They appear in culture as small bottle shaped budding yeasts only.

In summary, the numerous and significant differences listed above with respect to the two genera lead to the conclusion that there would be no reason to believe that an agent found to be effective with one (i.e. Candida) would also be effective against the other (Malassezia).

DETAILED DESCRIPTION OF A PREFERRED EMBODIMENT

I. Preparation of CSE

In general, CSE was prepared from commercially available chitin (Fluka, Sigma) as described in U.S. Pat. No. 4,701,444. A CSE composition for cosmetic or pharmaceutical use can be prepared at a concentration of 0.05–0.5% in a suitable carrier. Examples of carriers are various lotions, ointments and soaps.

II. In vitro inhibition of adhesion by CSE

The in vitro adhesion of M. furfur to human exfoliated corneocytes (skin epithelial cells) was investigated. Corneocytes were collected from healthy donors, suspended in PBS buffer with Triton, washed and standardized to $10^7$ cells/ml. M. furfur was grown at 37° C. on a solid medium (Sabouraud medium supplemented by yeast extract) containing olive oil and Tween 80. The fungal cells were suspended in PBS, washed and standardized to $10^7$ particles/ml. 0.5 ml of M. furfur suspension was mixed with 0.5 ml corneocytes and the mixture was incubated at 37° C. on a rotator for 2 hrs. Samples of the mixture were then fixed and stained (Gram stain), and adhesion of *M. furfur* to human corneocytes was determined.

Adhesion was assessed microscopically by counting the number of *M. furfur* yeast cells adhered to 50 corneocytes. Inhibition of adherence by CSE (25 mg/ml) was determined by comparing the number of adhering yeasts in mixtures containing CSE to the number in control mixtures devoid of CSE.

The results indicated that addition of CSE to the adhesion mixture reduced the number of fungi attached to the cells by approx. 40%.

In addition, the inhibitory effect of CSE was determined by a fluorometric assay using fluorescent labelled fungal cells and a microplate-fluorescence reader.

*M. furfur* culture suspensions were labelled with FITC. Following several washing steps (to remove excess FITC), the FITC-labelled yeast cells were added to the wells of microplates coated with a human keratinocyte cell line and containing or lacking CSE. The fluorescence was measured in a microplate-fluorescence reader. Inhibition was determined by comparing the fluorescence values of the wells containing CSE to those devoid of CSE (control wells).

The assay revealed inhibition values in the range of 40–80%. The values were CSE-concentration dependent.

III. In vivo treatment with CSE shampoo

A commercial shampoo containing 0.1% CSE was prepared. Ten subjects (5 males and 5 females, ages 30–69) suffering from Seborrheic dermatitis were treated with the shampoo. Each patient shampooed his hair twice, retaining the shampoo on the scalp for five minutes each time.

After one treatment nine of the subjects were cured. The tenth subject was cured after two treatments. The disease recurred in eight of the patients after approximately one month, while the remaining two patients were free of the condition for at least one month.

REFERENCES

1. Seborrheic Dermatitis, Psoriasis, Recalcitrant Palmoplantar Eruptions and Erythroderna. Andrew's Diseases of the Skin, 8th Ed. (1990) W. B. Saunders.
2. Ashbee, H. R., et al., Brit. J. Dermatol. 129: 533–540 (1993).
3. Danker et al., Rev. lnf. Dis., 9: 743 (1987).
4. Beachey, H., et al., Bacterial Adherence in Infectious Diseases. In: Current Concepts, pg. 1–52 (1982). A Scope Publication.
5. Segal, E. Microbiol. Sci. 4: 344–347 (1987).
6. Faergeman et al., Acta Derm. Res., 275: 246 (1983).
7. Simmons & Ahearn, Mycologia, 79: 38 (1987).

It will be appreciated by persons skilled in the art that the present invention is not limited to what has been thus far described, but rather the scope of the present invention is limited only by the following claims:

We claim:

1. A method for treating an infection caused by yeasts of genus Malassezia comprising a step of topically applying a formulation comprising a chitin soluble extract (CSE), optionally together with a suitable cosmetic carrier, to the area infected by or susceptible to infection by said yeasts, wherein said formulation is a soap or a shampoo.

2. A method according to claim 1 wherein said CSE is prepared from commercially available chitin.

3. A method according to claim 1 wherein said infection is seborrheic dermatitis.

4. A cosmetic formulation comprising an effective amount of a chitin soluble extract (CSE) for treating an infection caused by a yeast of genus Malassezia, optionally together with a suitable cosmetic carrier, wherein said cosmetic formulation is a soap or a shampoo.

5. A cosmetic formulation according to claim 4, wherein said CSE is prepared from commercially available chitin.

6. A cosmetic formulation according to claim 4, wherein said infection is seborrheic dermatitis.

7. A cosmetic formulation comprising an effective amount of a chitin soluble extract (CSE) for treating an infection caused by a yeast of genus Malassezia, together with a suitable cosmetic carrier, wherein said cosmetic formulation is a soap or a shampoo.

8. A cosmetic formulation according to claim 7, wherein said CSE is prepared from commercially available chitin.

9. A cosmetic formulation according to claim 7, wherein said infection is seborrheic dermatitis.

* * * * *